US00PP31852P3

(12) United States Plant Patent
Beatson

(10) Patent No.: US PP31,852 P3
(45) Date of Patent: Jun. 9, 2020

(54) HOP PLANT NAMED 'HORT9909'

(50) Latin Name: ***Humulus lupulus* L.**
Varietal Denomination: Hort9909

(71) Applicant: New Zealand Hops Limited, Nelson (NZ)

(72) Inventor: Ron Beatson, Motueka (NZ)

(73) Assignee: New Zealand Hops Limited, Nelson (NZ)

( * ) Notice: Subject to any disclaimer, the term of this patent is extended or adjusted under 35 U.S.C. 154(b) by 0 days.

(21) Appl. No.: 16/350,409

(22) Filed: Nov. 13, 2018

(65) Prior Publication Data

US 2019/0183001 P1 Jun. 13, 2019

Related U.S. Application Data

(60) Provisional application No. 62/596,294, filed on Dec. 8, 2017.

(51) Int. Cl.
*A01H 5/00* (2018.01)
*A01H 6/00* (2018.01)
*A01H 5/02* (2018.01)

(52) U.S. Cl.
USPC ..... Plt./236
CPC ..... *A01H 6/00* (2018.05); *A01H 5/02* (2013.01)

(58) Field of Classification Search
USPC ..... Plt./236
CPC ..... A01H 5/02; A01H 5/00
See application file for complete search history.

*Primary Examiner* — Kent L Bell
(74) *Attorney, Agent, or Firm* — Leydig, Voit & Mayer, Ltd.

(57) ABSTRACT

A new and distinct hop plant is described. The cultivar results out of selection from a population of seedlings derived from the deliberate crossing 'Hersbrucker Pure' (seed parent) (not patented) and 97.72-09 (pollen parent) (not patented). The new variety, 'Hort9909', is characterised by its cones maturing mid-season and having medium Alpha Acid and low cohumulone content. The new variety is suitable for beer flavouring.

4 Drawing Sheets

Genus and species of plant claimed: *Humulus lupulus* L.
Variety denomination: 'Hort9909'.

BACKGROUND OF THE INVENTION

The new cultivar of hop, *Humulus lupulus* L., was created in the course of a planned breeding program carried out at Motueka, New Zealand. It was selected from a population of seedlings derived from a cross made in 2004 between 'Hersbrucker Pure' (seed parent) (not patented) and 97.72-09 (pollen parent) (not patented). Seedlings from the cross were grown in a nursery at the same location during the 2004-5 season and subsequently planted in the field in 2005-06 season. In 2006, 'Hort9909' was identified as having potential as a new variety and given the breeder code 04.99-09. The variety was selected on the basis of its good agronomic performance, and chemistry profile.

SUMMARY OF THE INVENTION

A new and distinct hop plant is described. 'Hort09909' cultivar is characterised by having cones which are mid-season maturing and medium alpha acid and low cohumulone content. The new variety is suitable for beer flavouring.

In 2008-09, 'Hort9909' was asexually propagated via rhizome cuttings at Motueka, New Zealand. The resulting plants were found to be true to type demonstrating that the characteristics of the new variety 'Hort9909' are stable and transmitted without change through succeeding generations.

For three seasons, from 2009/10 to 2011/2012 'Hort9909' was trialled, for its commercial potential in a replicated plot trial. In 2012, it was decided to advance 'Hort9909' to larger-scale trialling, including brewing trials due to its agronomic and chemistry properties. Brewing trials were conducted over several seasons from 2012/13 to 2016/2017.

'Hort9909' is maintained at Motueka, New Zealand, where it has undergone observations for uniformity. All plants have been found to be true to type, that is, no off types have been observed. 'Hort9909' is distinguished from its parent female parent, 'Hersbrucker Pure' as 'Hort09909' has longer lateral cane length. The pollen parent, 97.72-09, is a male and thus does not produce cones. Under New Zealand growing conditions 'Hort9909' is distinguished from varieties of common knowledge by the following characteristics:

When grown in Motueka 'Hort9909' has stronger and earlier spring growth than 'Hort3829' (U.S. Plant Pat. No. 23,985). The cones of 'Hort9909' mature earlier than 'Rakau™' (not patented), 'Sticklebract' (not patented) and 'Dr Rudi™' (not patented) and are narrow ovate in shape where cones of 'Southern Cross' (not patented) are cylindrical.

BRIEF DESCRIPTION OF THE DRAWINGS

The accompanying photographs show typical specimens of the plant habit, cones, and leaves of the new cultivar as depicted in colours as nearly true as is reasonably possible to make the same in colour illustration of this character. The plants shown in these photopgraphs were two years old.

Figure 1:
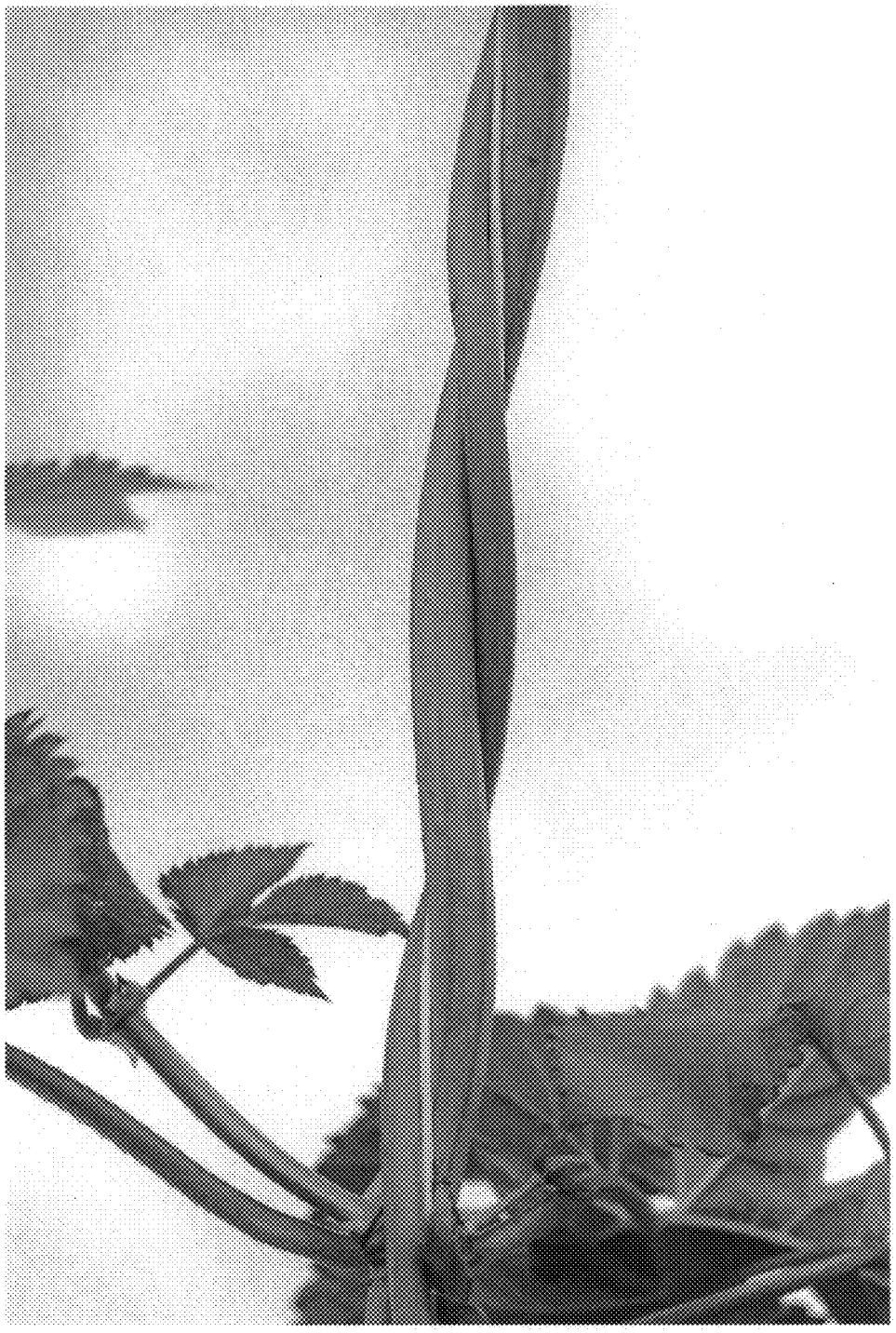
FIG. 1: close up of 'Hort9909' main shoot.
Figure 2:
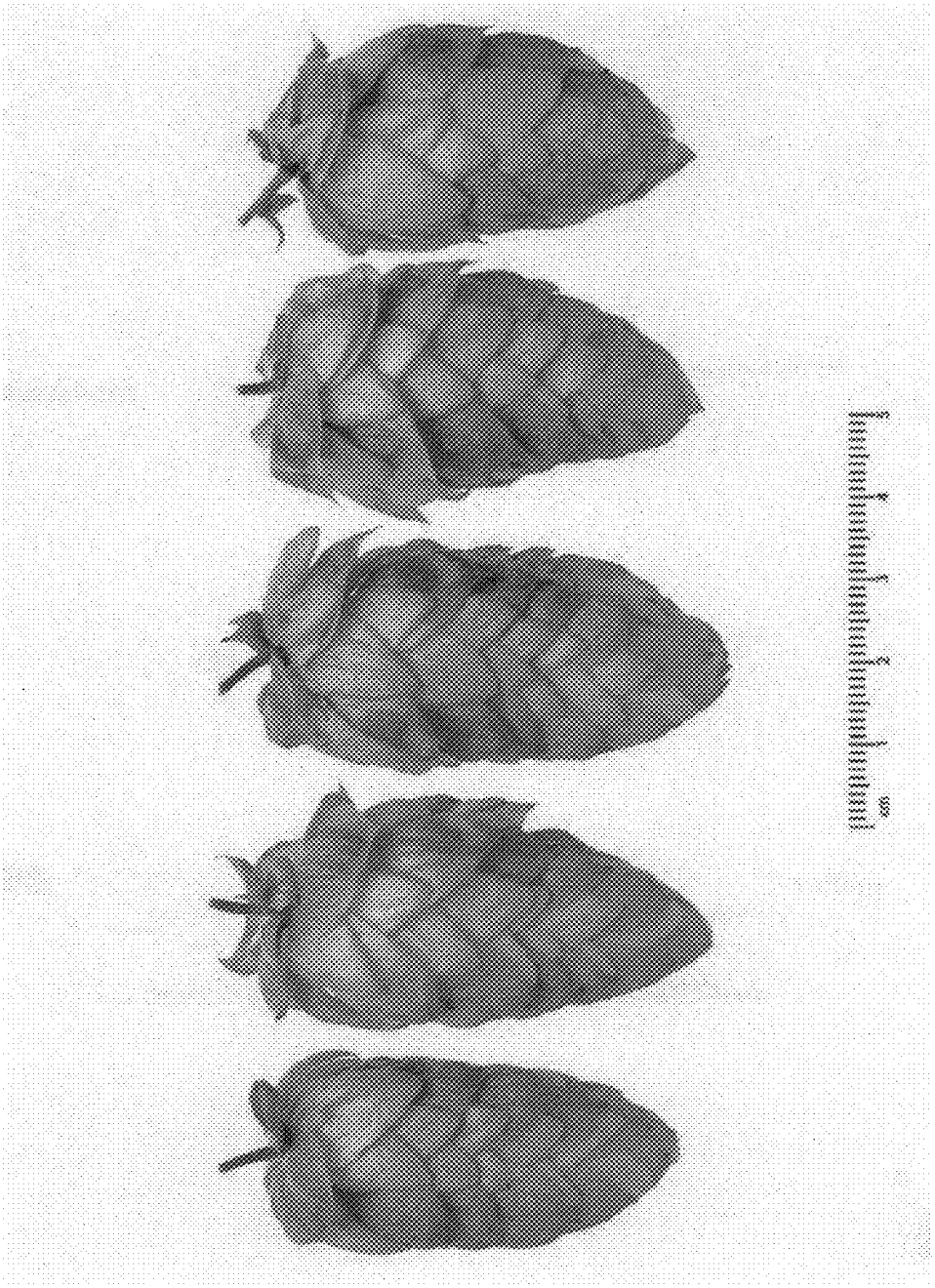
FIG. 2: 'Hort9909' cones in the studio.
Figure 3:
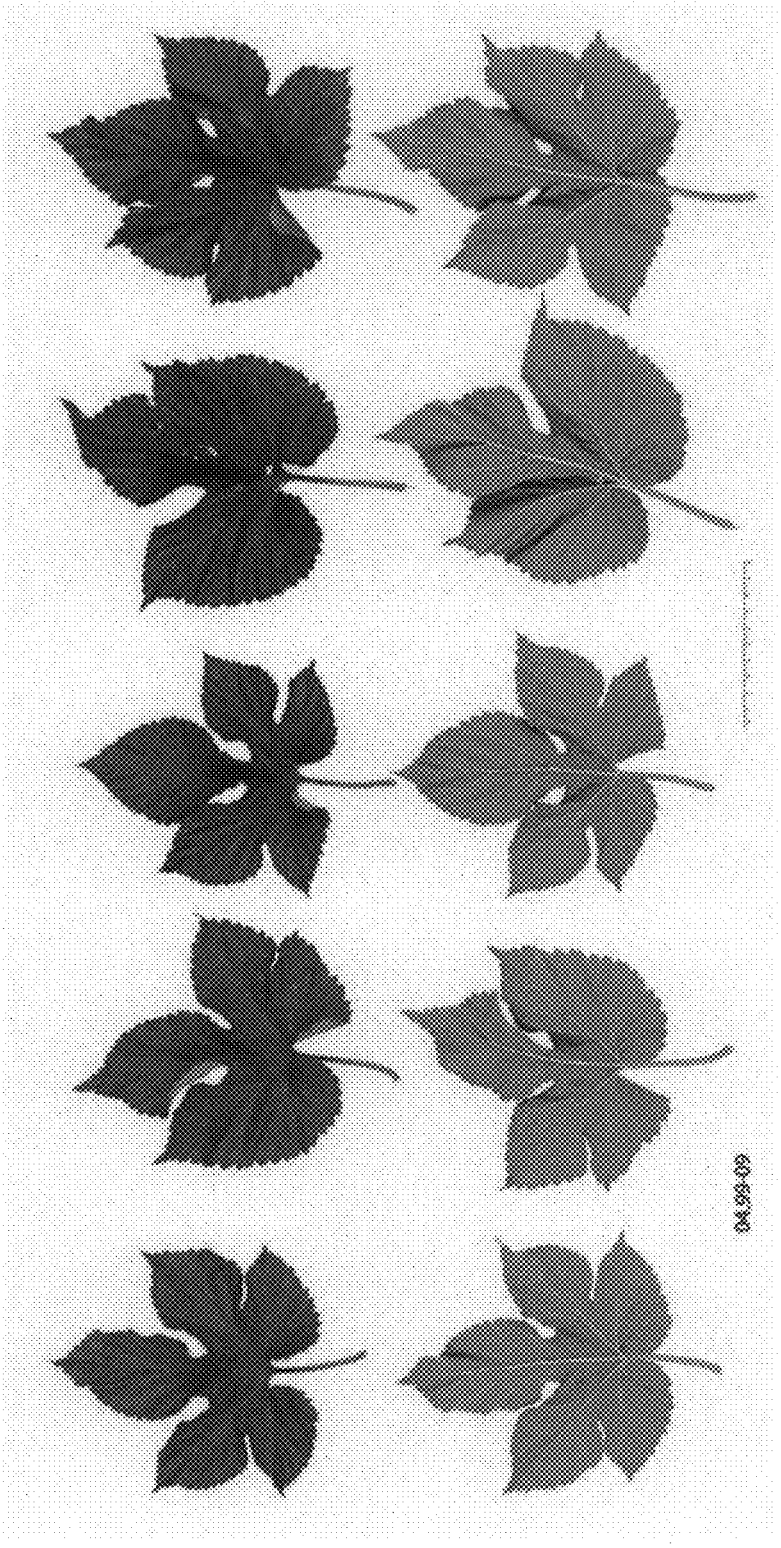
FIG. 3: Upper and underside of 'Hort9909' leaf
Figure 4:
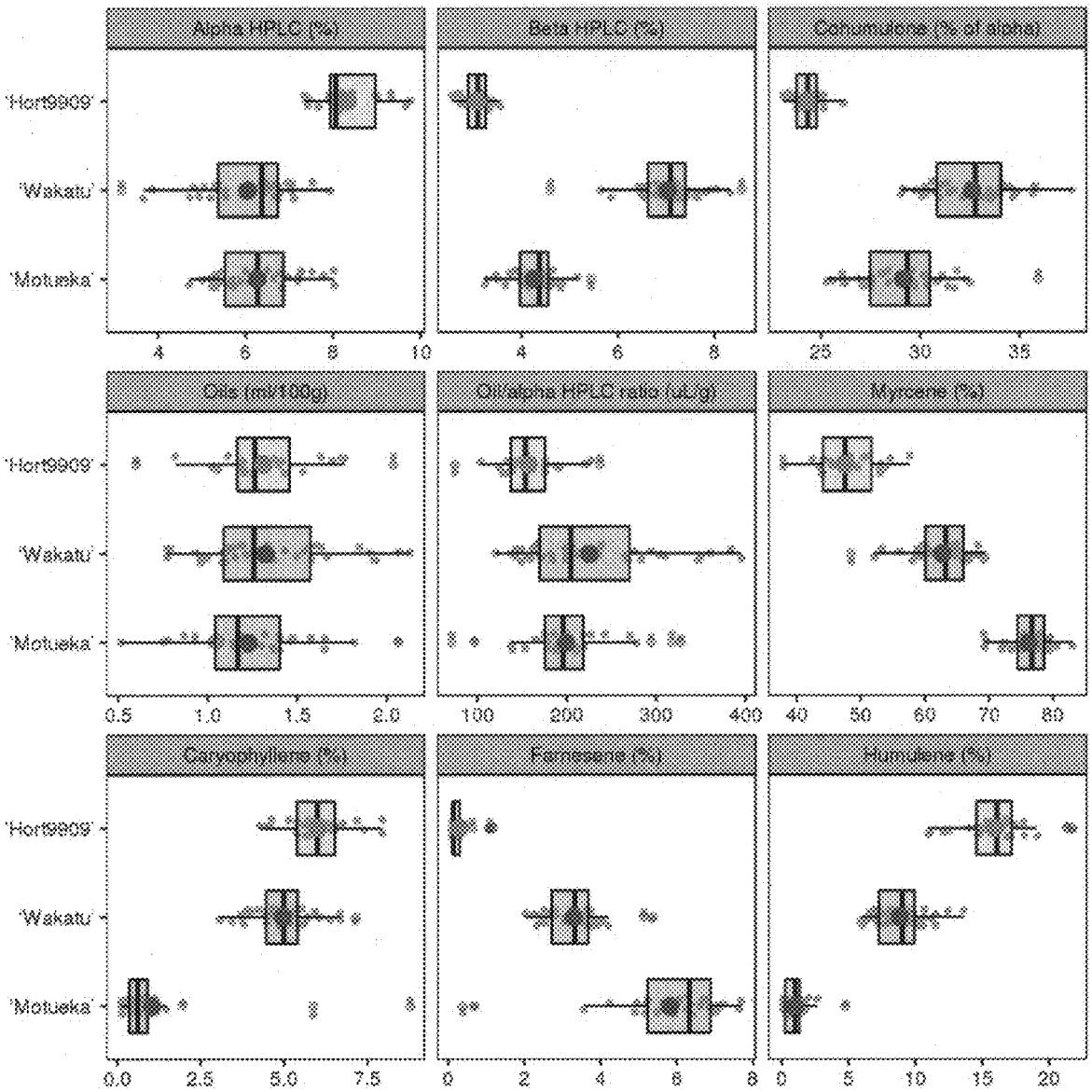
FIG. 4. Mean of at harvest chemistry profiles for 'Hort9909', 'Wakatu™' (not patented) and 'Motueka™' (not patented).

Trials and testing were conducted in Motueka, New Zealand.

BOTANICAL DESCRIPTION

The following is a description of the new cultivar with colour terminology in accordance with The Royal Horticultural Society Colour Charts (R.H.S.C.C.) 2001 edition. The specimens described were two years old and were grown at Motueka, New Zealand. The observations were made over the 2014-2017 seasons.

Plant form and vigour: Mature plants had normal growth type and produced a yield (averaging 1.8-2.2 tonnes/ha,) of mid-season maturing cones. The plant shape was cylindrical with a medium head volume. The main shoot of a one year old plant, had an average vine diameter half way up the vine of 8 mm, and anthocyanin coloration of the stem was weak or almost absent. Node pubescence was weak. The average internode length was 200 mm. Internode Bine length was 20 cm and Bine colour was 138B.

Laterals: The side shoots from the middle third of the plant were medium to long in length, an average of approximately 75 cm, and produced a medium number of cones, an average of 3 per node. The side shoots from the top third of the plant had an average length of 75 cm and produced an average of 30 cones per lateral. Stipule pose is drooping, stipule colour is 144B, and the number of stipules per node is 2.

Leaves: The leaves were lobed with predominantly five lobes. The large, weakly blistered leaves were alternate with crenate margins. The upper leaf surface colour was near, Green, 139A and the intensity of colour light to medium. The lower leaf surface colour was N138B. The average leaf size was 139 mm in length and 165 mm in width. Venation pattern is palmatifid and venation colour is 143B. Petioles have an average length of 100 mm, an average width of 4.1 mm, and are near green 143B.

Cones: were medium-large in size and narrow-ovate in shape in longitudinal section; in cross section they were square in shape. The cones average length was 44 mm and average width 23 mm. Average cone weight was 150-170 mg (dry). Bracts were medium in size, with an average length 16 mm and average width 11 mm, slightly open and had a short apex. The shape of the tip of the bract is narrowly obtuse, and the colour of the bracts was 137C. Bracteole had an average length of 17 mm and average width 10 mm. Bracteole shape was ovate, and the color of the bracteole was N144A. Strigs were long, approximately 25 mm, with an average width of 3 mm. The colour of the strig was Green, near N143D.

Physiological timing: Flowering commences late in Motueka, New Zealand around the 26 January. Harvest is mid-season in the New Zealand season, commencing mid to late March, under normal conditions.

Chemistry profile: 'Hort9909' has undergone extensive chemistry profile testing. 'Hort'9909' has Alpha Acid levels of around 7-9.5%, Beta Acid levels of around 3-4% and Cohumulone levels around 24-25%.

HPCL & oil composition (measured within 6 months of harvest, stored at 0° C.):

| | |
|---|---|
| Alpha acids (HPLC) | 8.2% |
| Beta acids (HPLC) | 2.8% |
| Cohumulone content (% total alpha acids) | 24% |
| Total oils (mls/100 g) | 1.3% |
| A-Pinene, | 0% |
| B-Pinene, | 0.7% |
| Myrcene. | 48% |
| 2-methyl-butyl iso butyrate, | nt |
| Limonene, | 1.3% |
| Linalool, | .3% |
| Caryophyllene, | 6% |
| B-Ionone, | nt |
| Geraniol, | 1.6% |
| Nerol, | nt |
| Farnesene, | 0.2% |
| Humulene, | 16% |
| Citral, | nt |
| Geranyl Acetate, | 0.3% |
| Cilronellol | nt |

Where: nt = not measured

Use: primarily flavouring and bittering ingredient for beer.

Pest and disease: 'Hort9909' does not appear particularly resistant or susceptible to any particular pests or diseases known to afflict *Humulus lupulus*.

Hardiness: The plant cold hardiness according to the American zone classification has not been determined.

The invention claimed is:

1. A new and distinct hop plant substantially as described and illustrated herein.

* * * * *